(12) United States Patent
Hemming et al.

(10) Patent No.: US 6,985,768 B2
(45) Date of Patent: Jan. 10, 2006

(54) PHYSIOLOGICAL EVENT DETECTION

(75) Inventors: Michael T. Hemming, Kiowa, CO (US); John R. Hamilton, Littleton, CO (US); Daniel L. Hansen, Castle Rock, CO (US); Kent Samuelson, Parker, CO (US)

(73) Assignee: Medtronic, Inc., Minneaolis, MN (US)

( * ) Notice: Subject to any disclaimer, the term of this patent is extended or adjusted under 35 U.S.C. 154(b) by 280 days.

(21) Appl. No.: 10/376,920

(22) Filed: Feb. 28, 2003

(65) Prior Publication Data
US 2004/0171953 A1 Sep. 2, 2004

(51) Int. Cl.
*A61B 5/402* (2006.01)

(52) U.S. Cl. ...................... 600/509; 600/513
(58) Field of Classification Search .............. 607/1–28; 600/508–547
See application file for complete search history.

(56) References Cited

U.S. PATENT DOCUMENTS

| | | |
|---|---|---|
| 4,450,527 A | 5/1984 | Sramek ...................... 364/415 |
| 4,702,253 A | 10/1987 | Nappholz et al. |
| 5,273,049 A | 12/1993 | Steinhaus et al. ........... 128/696 |
| 5,282,474 A | 2/1994 | Valdès Sosa et al. ....... 128/670 |
| 5,361,776 A | 11/1994 | Samuelson et al. |
| 5,560,368 A | 10/1996 | Berger ........................ 128/703 |
| 5,676,153 A | 10/1997 | Smith et al. ................ 128/702 |

FOREIGN PATENT DOCUMENTS

EP 0 173 714 B1 6/1990

*Primary Examiner*—Scott M. Getzow
(74) *Attorney, Agent, or Firm*—Girma Wolde-Michael; Michael C. Soldner

(57) ABSTRACT

In general, the invention is directed to techniques for electrically detecting physiological events. The physiological events may include cardiac events such as R waves or p waves. In addition, the physiological events may include respiratory events. In general, the techniques involve converting an analog physiological signal to a digital delta value, correlating the digital delta value with a correlation template, and detecting a physiological event based on an output of the correlation. A digital correlation-based technique, as described herein, is implemented to reliably detecting physiological events, particularly for very small signals captured in the presence of significant background noise.

45 Claims, 10 Drawing Sheets

PHYSIOLOGICAL EVENT DETECTION

TECHNICAL FIELD

The invention relates to medical devices and, more particularly, to detection of physiological events.

BACKGROUND

Many diagnostic and therapeutic medical devices are equipped to electrically detect physiological events. Such devices may incorporate, for example, intracardiac, subcutaneous, or surface detection components. In some devices, detection of a physiological event is followed by delivery of a therapy or collection of diagnostic data.

In response to detection of a cardiac event, for example, certain medical devices deliver pacing therapy or a high energy antidysrhythmic shock, collect diagnostic data, or both. Some diagnostic and therapeutic electrical medical devices are also equipped to electrically detect respiration. In this case, a device may use detection of respiration as an indication of patient activity level to drive rate-responsive pacing.

To reliably detect physiological events, medical devices generally need to sense very small electrical signals, e.g., on the order of 10 microvolts to 100 millivolts. In addition, the medical device should be capable of discriminating physiological events in the presence of noise. Noise sources may include random device noise, electrode or environment noise, conducted sine wave noise including 50–60 Hz noise, and motion artifact type noise. Noise can make it difficult to reliably detect a physiological event.

SUMMARY

The invention is directed to techniques for electrically detecting physiological events. The physiological events may include cardiac events, such as R waves or p waves. Alternatively, the physiological events may include respiratory events. In general, the techniques involve converting an analog physiological signal to a digital delta value, correlating the digital delta value with a correlation template, and detecting a physiological event based on an output of the correlation. A digital correlation-based technique, as described herein, could be effective in reliably detecting physiological events, particularly for very small signals captured in the presence of significant background noise.

In one embodiment, the invention provides a physiological event detector comprising a delta conversion circuit, a correlation circuit and an event detection circuit. The delta conversion circuit converts an analog physiological signal to a digital delta value. The correlation circuit correlates the digital delta value with a correlation template. The event detection circuit detects a physiological event based on an output of the correlation circuit.

In another embodiment, the invention provides a method comprising converting an analog physiological signal to a digital delta value, correlating the digital delta value with a correlation template, and detecting a physiological event based on an output of the correlation In a further embodiment, the invention provides a physiological event detector comprising means for converting an analog physiological signal to a digital delta value, means for correlating the digital delta value with a correlation template, and means for detecting a physiological event based on an output of the correlation.

The invention provides one or more advantages. For example, a detector constructed in accordance with the invention may provide reliable detection of physiological events, such as cardiac or respiratory events. Also, respiratory events may be detected without measuring a response to an injected stimulus. Because the respiratory event detection generally involves a measurement of peak QRS complex signal deltas, the respiration signal does not require a stimulus. This aspect of the respiratory event detection could reduce energy consumption, complexity and potential physiological side effects such as inadvertent stimulation of the heart caused by application of the measurement stimulus.

In addition, the structure and operation of the detector, in general, provides substantially reduced power consumption, reduced complexity, and ease of manufacturability. In particular, the detector could be configured to implement digital processing techniques that require relatively few external components and thereby permit ready integration of circuit components. The digital processing techniques also may permit reduced current consumption. As a further advantage, the detector implements adaptive thresholds that conform to different detection conditions.

The details of one or more embodiments of the invention are set forth in the accompanying drawings and the description below. Other features and inventive aspects will be apparent from the description and drawings, and from the claims.

DETAILED DESCRIPTION

Figure 1:
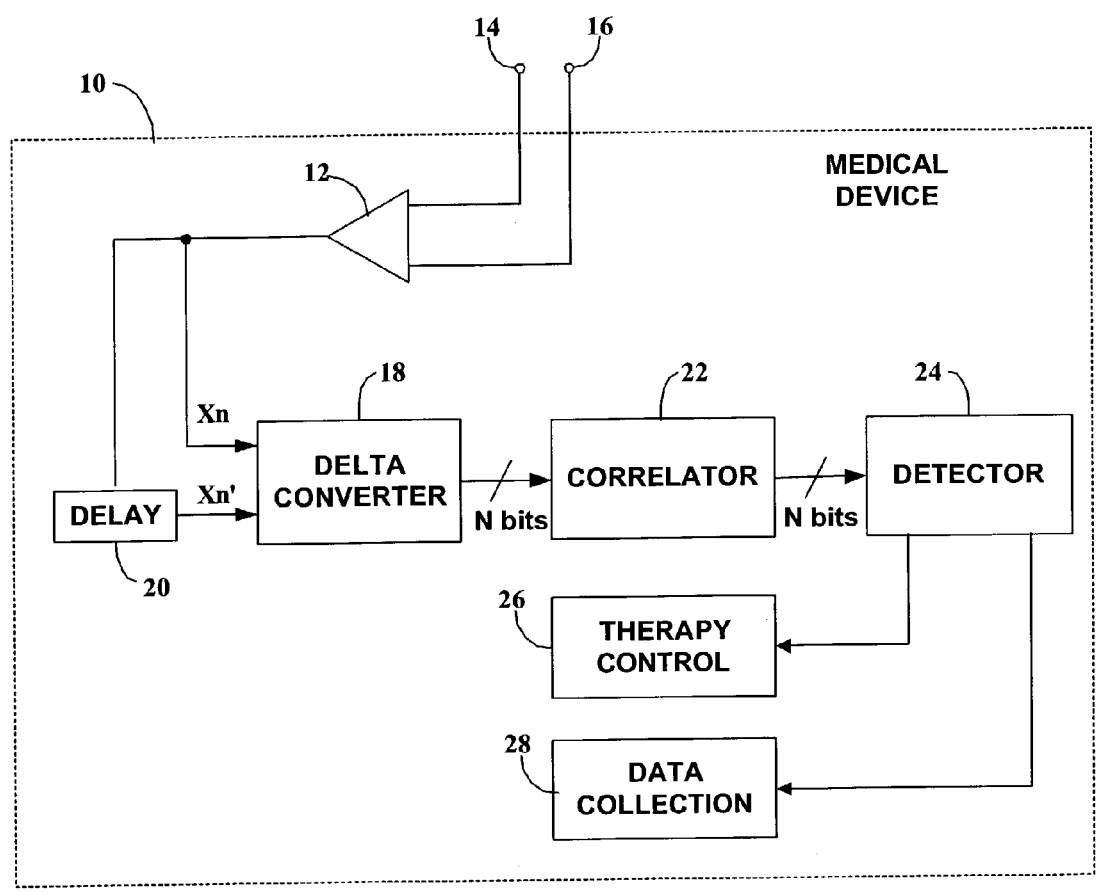
FIG. 1 is block diagram of an exemplary device for electrically detecting physiological events.

FIG. 1 is block diagram of a device 10 for electrically detecting physiological events. As will be described, device 10 may be configured to electrically detect physiological events using digital correlation techniques. Digital correlation-based techniques, as described herein, are effective in reliably detecting physiological events, particularly for very small signals captured in the presence of significant background noise. In addition, device 10 is readily manufacturable and suitable for low power implementations.

Device 10 may form part of an implanted medical device or an external medical device. In other words, device 10 may be implanted within a patient by itself or in conjunction with other implanted therapeutic or diagnostic devices such as pacemakers, cardioverter/defibrillators, drug delivery device, neurostimulators, loop recorders, and the like. Alternatively, device 10 may reside within an external device that obtains physiological signals from a patient.

As shown in FIG. 1, device 10 includes an input amplifier 12 that senses physiological signals via two or more electrodes 14, 16. Electrodes 14, 16 may be implemented as intracardiac electrodes, e.g., on implanted leads, or as surface or subcutaneous electrodes. Electrodes 14, 16 may be arranged in unipolar or bipolar arrangements. In an implanted embodiment, for example, one of electrodes 14, 16 could be formed on a housing associated with device 10.

In the example of FIG. 1, device 10 further includes a delta converter 18 that converts an analog physiological signal received across electrodes 14, 16 to form an N-bit digital word representing a delta value. Delta converter 18 may be realized by a high gain comparator-based delta modulation circuit or a high gain analog-to-digital converter. To adequately span the input range and slews in the input signal received across electrodes 14, 16, delta converter 18 is selected to provide sufficient bit depth, e.g., with N=12 or greater. The digital delta value represents a slope, i.e., first derivative, between sample Xn and a delayed sample Xn' (20). If the input signal across electrodes 14, 16 is processed through a high gain analog-to-digital converter, the signal could be converted to the delta value using a first order differential equation.

A digital correlator 22 correlates the delta value with a correlation template to produce an N-bit correlation output. In general, correlation is a weighted moving average between two signals. One signal provides the weighting function, and the other is the input signal. Each point in a signal is multiplied by the corresponding element of the other signal. The signals are shifted one point with respect to each other and re-multiplied. The multiplied points are summed (integrated) to obtain the result of the correlation. Correlation is a maximum when two signals are similar in shape, and are in phase. When the two signals are similar in shape and aligned with respect to each other, their product is positive.

As will be described in further detail, correlator 22 performs a dot product of an input vector formed by the delta value and a slope template vector formed by a correlation template. An event detector 24 detects a physiological event based on the correlator output. Event detector 24 applies threshold, peak or slope discrimination functions, for example, to detect selected physiological events.

When a particular physiological event is detected, event detector 24 sends a detection signal to a therapy control circuit 26, a data collection circuit 28 or both. Therapy control circuit 26 triggers delivery of a therapy such as a cardiac stimulation pulse or shock in response to the detection signal. Similarly, data collection circuit 28 triggers collection of data such as capture of a cardiac waveform in response to the detection signal generated by event detector 24.

Figure 2:
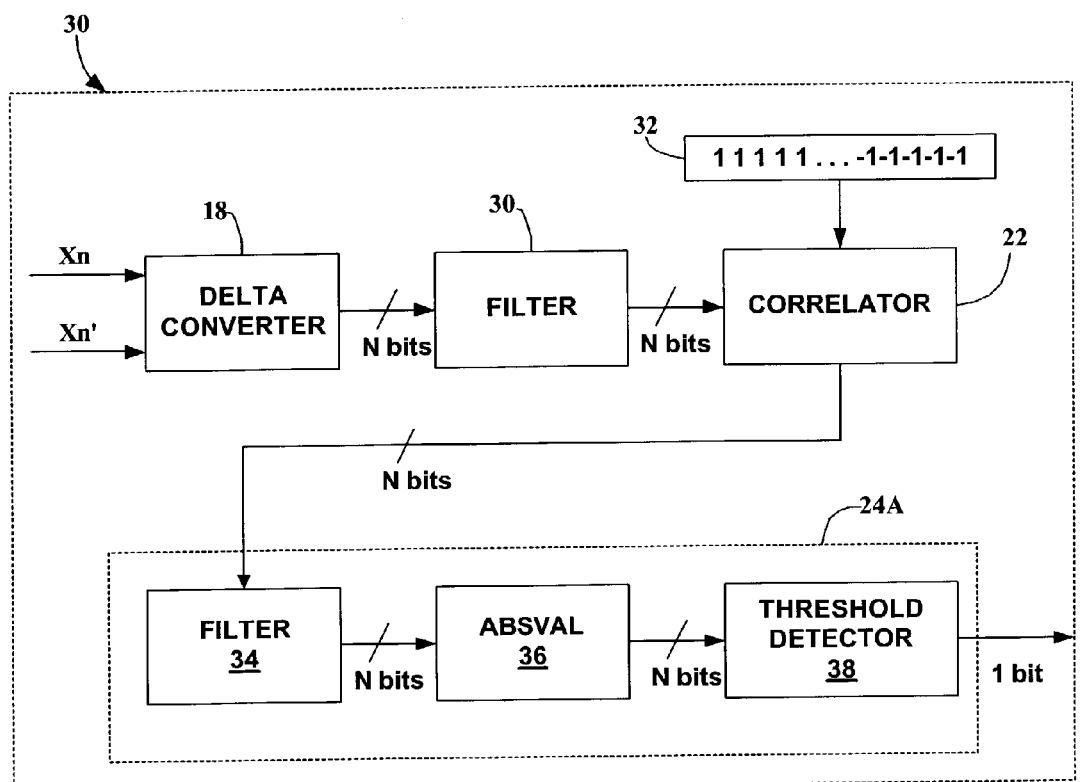
FIG. 2 is a block diagram of an exemplary device for electrically detecting cardiac R wave events.

FIG. 2 is a block diagram of a device 30 for electrically detecting cardiac R wave events. Device 30 includes an event detector 24A. Electrical detection of a cardiac R wave, which represents a ventricular contraction, may be useful in therapy control, data collection, or both. For example, indication of an R wave could be followed by delivery of pacing therapy, high energy antidysrhythmic shock or diagnostic data collection. Device 30 generally conforms to device 10 of FIG. 1, but depicts additional components that could be added. For example, device 30 of FIG. 2 further includes a filter 30 that filters the delta values produced by delta converter 18. In particular, filter 30 is realized by a low order digital smoothing filter. Filter 30 could be effective in removing some of the high frequency noise transients that may be present in the delta value. To avoid non-linear phase delay, filter 30 may be realized by a tapped finite impulse response (FIR) low pass digital filter.

FIG. 2 also illustrates a correlation template 32 used by correlator 22. Correlator 22 performs a correlation between the filtered delta value from delta converter 12 and correlation template 32 to produce an N-bit correlation output. Correlator 22 receives the delta value, with optional smoothing by filter 30, and performs a dot product operation with correlation template 32 to produce a correlation output. The delta value forms an input vector $[b_i, b_{i-1}, \ldots _{i-W}]$ for correlation with the correlation template vector $[[1 \ 1 \ \ldots \ 1]_{W/2} \ [-1 \ -1 \ \ldots \ -1]_{W/2}]$. Correlation template 32 forms a slope template vector. The width of template 32 may be fixed and selectable depending on signal type. For intracardiac signals, for example, the template width may be on the order of 30 ms.

The output of correlator 22 is the sum of the product between correlation template 16 and the delta value over the previous W samples. The correlation template vector used in cross-multiplication with the delta value input vector is selected such that the product of the two vectors has the largest positive value when the input vector represents a maximum positive slope within a W/2 window followed by a maximum negative slope within a W/2 window, or vice versa.

Thus, the correlation template may be referred to as a weighting function, characterized by a series of +1s followed by a series of −1s. When the weighting function is aligned with the peak of the R wave, the positive deltas are multiplied by +1 and the negative deltas are multiplied by −1, and the sum of these two products provides a positive number for maximum filter output. As the weighting function is 'correlated' with the delta signal, portions that match the template will be amplified and portions that do not match will not be amplified. The pairing of maximum, oppositely signed slopes, corresponds to detection of a cardiac event.

The length, W, of the correlation template may be modified according to the character of the input signal. For example, intracardiac events, and especially atrial events, typically have a shorter duration. In this case, W is selected to be narrower. Normal sinus surface and subcutaneous events typically have a longer duration and may require a wider W. Ectopic events, including fibrillations, premature contractions and paced events, tend to be relatively long in duration and could accommodate a very wide W.

Mathematically, the function implemented by correlator 22 can be expressed as a difference equation as follows:

$$Y_n = \sum_{n=0}^{M} x_n - \sum_{n=M+1}^{2*M} x_n. \tag{1}$$

In the above equation (1), Yn is the output of the correlator 22 and Xn is the input delta value applied to the filter. In theory, correlator 22 adds samples 0 through M and subtracts samples M through 2M to produce the filter output. This corresponds to M samples of positive slope followed by M samples of negative slope, as represented by the correlation template vector $[[1 \ 1 \ \ldots \ 1]_{W/2} \ [-1 \ -1 \ \ldots \ -1]_{W/2}]$. If the sampling rate is 1000 Hz, for example, and M is 20, then correlator 22 amplifies 20 mS of positive slope followed by 20 mS of negative slope. For implementation, the collection of repeated summing degenerates to a 3-term accumulation with coefficients −1, 2 and −1.

Device 30 may be configured to detect physiological events by sensing very small signals obtained, for exampled, from intracardiac, subcutaneous or surface electrodes. The signals may be on the order of 10 microvolts to 10 millivolts. In addition, device 30 should be capable of discriminating the physiological events in the presence of noise, which may be caused by random device noise, electrode or environment noise, conducted sine wave noise including 50–60 Hz noise, and motion artifact type noise.

A filter 34 filters the correlation output. Filter 34 smoothes out the correlation output using a summing or averaging window to reduce effects of input noise. In some embodiments, filter 34 is selected to have a width of approximately 15–20 ms to effectively cancel 50 and 60 Hz input noise. This type of noise is typically in the form of conducted sine waves producing effects that can be mitigated over a given summing or averaging interval. The approximate 15–20 ms window also may be effective in reducing conduced sine waves with periods within a multiple of 15–20 ms. Random noise also is reduced by summing or integrating the correlation output using filter 34.

An absolute value (ABSVAL) circuit 36 produces an absolute value of the filtered correlation output and applies the absolute value to a threshold detector 38. The absolute value operation is especially useful if the input electrode vector/direction is not known to produce large positive R or p waves.

Threshold detector 38 compares the absolute value of the filtered correlation output to a threshold value. In the event the correlation output exceeds the threshold value, threshold detector 38 generates a detection signal. In the example of FIG. 2, the threshold is selected to discriminate a correlation output corresponding to a cardiac R wave. The threshold used by threshold detector 38 may be a fixed, programmable threshold. Alternatively, the threshold may vary according to the input. In particular, the threshold adapts to the magnitude of the absolute value applied to threshold detector 38 from absolute value circuit 36. Inputs that vary quickly during fibrillation or deep respirations may be more effectively tracked by adapting the threshold to changes in the input signal.

The threshold is defined by a peak value determined by the local maximum of the correlation output, and a rate of decay. For example, the threshold may be set to decay at a programmable rate with the decay target being 0. However, the threshold is never allowed to reach zero. Instead, a measure of the input signal can be added back into the threshold value to increase the threshold, i.e., by applying a threshold "add-back." In this way, a margin is maintained between the subthreshold noise and the threshold level so that only large, quickly appearing peaks within the correlation output will be recognized as an indication of a cardiac event. Consequently, threshold detector 38 detects intervals of systole, that are characterized by an unusually long period of time without cardiac events.

As an example, an adaptive threshold is set at 50% of the previous peak output of correlator 22. Otherwise, when the correlator output is less than the threshold, the threshold decays exponentially in order to track lower amplitude signals. In addition, a portion of the sub-threshold signal is added back into the threshold value to prevent it from decaying too rapidly if the signal is noisy. The intention of this threshold add-back feature is to make the threshold 'float' above the noise, and only allow fast moving transitions to exceed the threshold and indicate an R wave detection. In an exemplary embodiment, an adaptive threshold value can be represented by a discrete difference equation as follows:

$$Y_n = (1-k_1)*Y_{n-1} + k_2*X_n. \qquad (2)$$

In the above equation (2), $Y_n$ represents the threshold value, which is the sum of the last threshold signal, $Y_{n-1}$, and the present correlator output, $X_n$. Two constants, $k_1$ and $k_2$, determine the threshold value. A value of 0.001 may work well for $k_1$, the decay factor, and a value of 0.002 may work well for $k_2$, the add-back factor. The calculation of the threshold signal may be made for every data sample, i.e., delta value, produced by delta converter 12.

Figure 3:
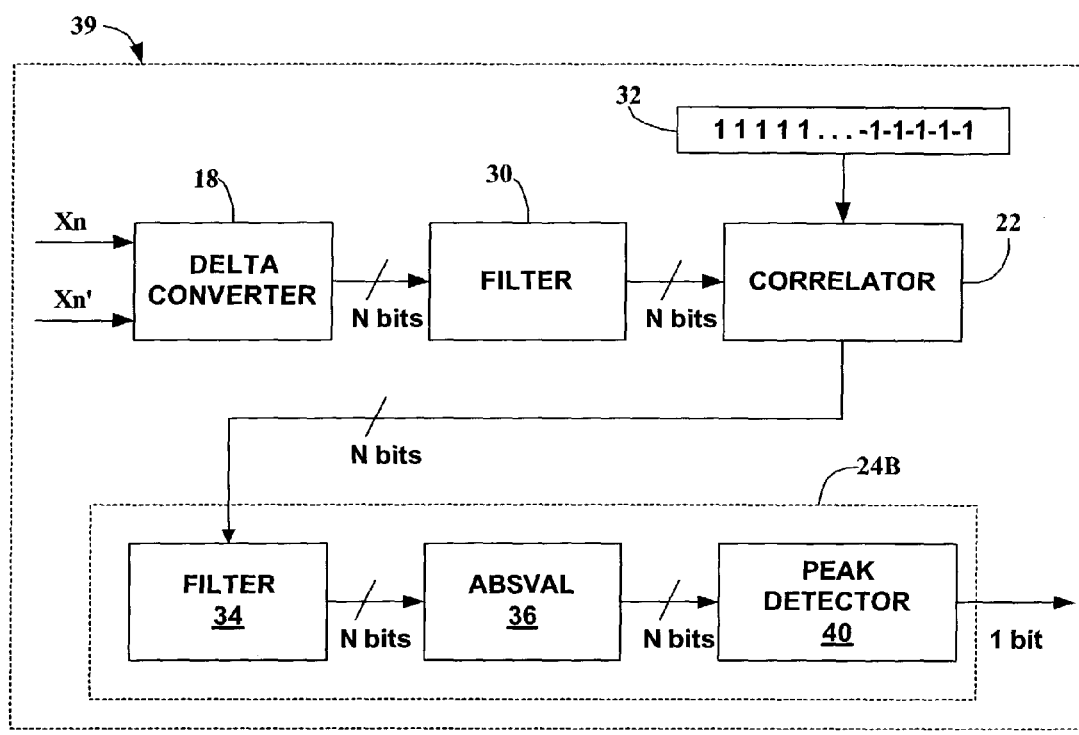
FIG. 3 is a block diagram of an exemplary device for electrically detecting respiratory events.

FIG. 3 is a block diagram of a device 39 for electrically detecting respiratory events. Device 39 includes an event detector 24B. Notably, in accordance with the invention, respiratory events is detected without measuring a response to an injected stimulus. Because the respiratory event detection generally involves a measurement of peak QRS complex signal deltas, the respiration signal does not require a stimulus. This aspect of the respiratory event detection may reduce energy consumption, complexity and potential physiological side effects such as inadvertent stimulation of the heart caused by application of the measurement stimulus.

Electrical detection of respiration is useful in therapy control, data collection, or both. For example, respiration is one of the indicators used to determine patient activity level. In particular, fast breathing may correlate to high activity levels, whereas slow breathing may correlative to periods of inactivity or rest. Device 39 conforms substantially to device 30 of FIG. 2. For example, device 39 includes delta converter 18, filter 30, correlator 22, filter 34 and absolute value circuit 36. Device 29 further includes, however, a peak detector 40 to resolve peaks in the correlation output generated by correlator 22.

Peak detector 40 analyzes the correlation output to detect a peak of the output over a period of time, and detects a respiratory event in response to detection of the peak. In effect, peak detector 40 measures the size of a derivative of the input cardiac signal to develop an indication of respiration. The specific derivative is a varying peak value of the cross-multiplied product of the digital delta value and correlation template 32. As in the example of FIG. 2, correlation template 32 is selected to produce large correlation output when presented with a cardiac event such as a surface R wave or atrial intracardiac p wave. In particular, correlation template 32 provides a slope template vector $[[1\ 1\ \ldots\ 1]_{W/2}\ [-1\ -1\ \ldots\ -1]_{W/2}]$.

The product of the delta value input vector $[b_i, b_{i-1}, \ldots b_{i-W}]$ and the slope template vector $[[1\ 1\ \ldots\ 1]_{W/2}\ [-1\ -1\ \ldots\ -1]_{W/2}]$ provided by correlation template 32 has the largest positive value when the delta value presents a maximum positive slope within a W/2 window followed by a maximum negative slop within a W/2 window. Again, the pairing of maximum, oppositely signed slopes correlates with a cardiac event such as an R wave or p wave. As in the example of FIG. 2, the length, W, of correlation template may be modified according to the characteristics of the input signal.

Filter 34 filters the correlation output, and absolute value (ABSVAL) circuit 36 produces an absolute value of the filtered correlation output. Peak detector 40 tracks the level of the correlation output to obtain a rising and falling indication of respiration. In particular, peak detector 40 is configured to monitor the correlation output over a period of time to identify peaks.

When the correlation output reaches a peak, peak detector 40 detects a respiration event. In response, peak detector 40 generates a respiratory event detection signal. Peak detector 40 transmits the respiratory event detection signal to a therapy control circuit 26 or data collection circuit 28 as shown in FIG. 1. In this manner, the respiration activity electrically detected by device 39 could be used to control therapy, e.g., rate-responsive pacing, or collection of diagnostic data. Also, the electrically detected respiration activity may be used in conjunction with detection of physical activity level by other activity sensors to evaluate a patient's response to activities of daily living. Again, device 39 permits detection of respiratory events without the need to apply a stimulus. Instead, device 39 relies on analysis of the paced or intrinsic cardiac response to detect respiratory events. This technique is particularly useful for respiration cycle length extraction for non-uniformly sampled events.

Figure 4:
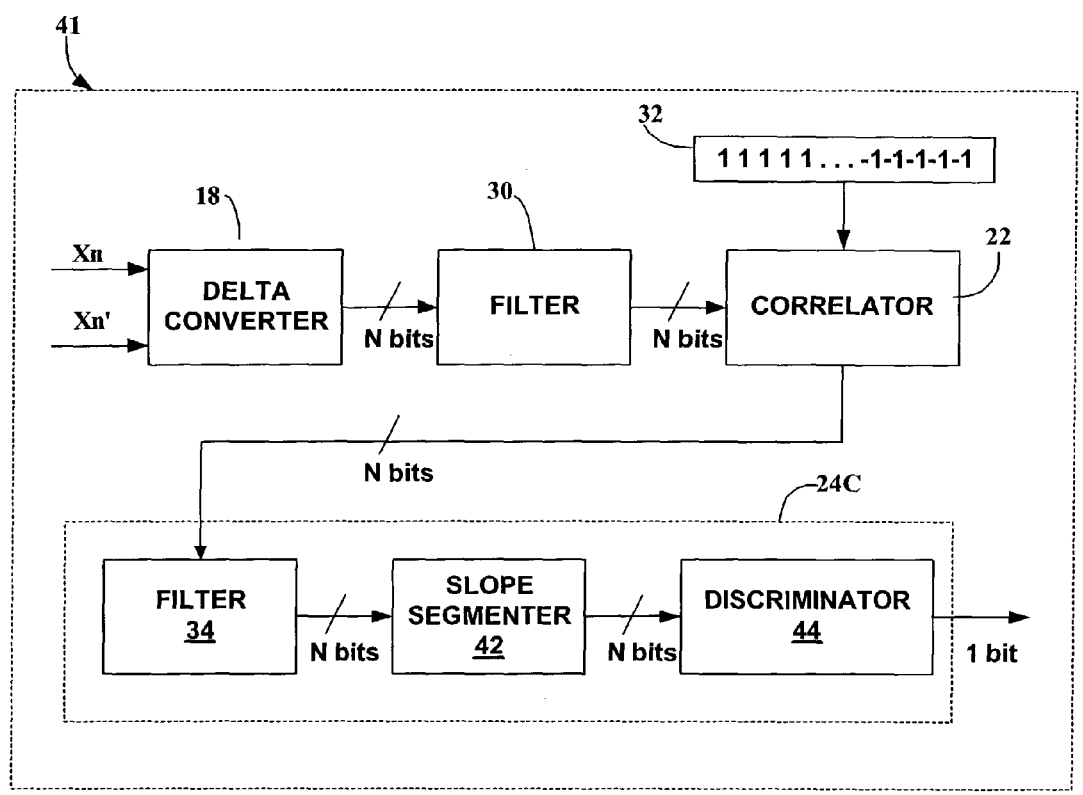
FIG. 4 is a block diagram of an exemplary device for electrically detecting cardiac p wave events.

FIG. 4 is a block diagram of a device 41 for electrically detecting cardiac p wave events. Device 41 includes an event detector 24C. Electrical detection of a cardiac p wave, which represents atrial contraction, could be useful in therapy control, data collection or both. For example, indication of a p wave is used to assist rhythm classification, create atrial-responsive VVI pacemakers, or provide trending diagnostics. Discriminating p waves from far-field R waves in an atrial signal can be difficult, however, due to similar amplitude information.

Device 41 conforms generally to devices 30, 39 of FIGS. 2 and 3, respectively. Device 41 further includes, however, a slope segmenter 42 and a discriminator 44, and does not include an absolute value circuit or a threshold or peak detector. Slope segmenter 42 classifies the correlation output from correlator 22 in terms of the slope of the waveform. In particular, slope segmenter 42 classifies the correlation output according to a plurality of different slope ranges. Based on the classification assigned to the correlation output, discriminator 44 detects a p wave event. The techniques for p wave detection described herein may be especially in conjunction with surface of subcutaneous electrodes that tend to produce p waves that become smaller or similar in magnitude to other complexes in the cardiac waveform.

Slope segmenter 42 classifies segment of an input waveform provided by the correlation output into m levels of like slope. For example, in a simple embodiment, slope segmenter 42 classifies the correlation output into three segments: increasing (+1), flat (0), and decreasing (−1). Slope segmenter 42 operates by comparing the output of filter 34 to programmable thresholds. Filter 34 may be a summing or averaging filter. The width of filter 34 may be programmable and adjusted to match the width of the input signal characteristics. In particular, the width of filter 34 is adjusted to match a portion of the approximate width of a cardiac p wave. By adjusting the width of correlator 22, greater discrimination among dissimilar cardiac events are realized.

Discriminator 44 analyzes the output of slope segmenter 42 to identify slope patterns that correspond to cardiac p waves. The patterns can be found in the input waveform and the output of correlator 22. Discriminator 44 may be configured to identify p waves based on the widths of classified slope segments. Attention to particular widths permits discrimination of p waves vis-a-vis other cardiac events such as far-field R waves.

In some embodiments, discriminator 44 may be configured to generate an estimate of the mean atrial rate, or time interval between p waves. The estimate of mean atrial rate can be used to further discriminate and exclude unlikely p wave candidate segments from the input waveform. In other words, segments that appear as p waves are discarded if they are inconsistent with the estimated mean atrial rate, thereby making discrimination even more selective. Estimates of mean atrial rate may be expected to vary on a beat-to-beat basis and exhibit progressive rate increases and decreases with varying patient activity levels.

Figure 5:
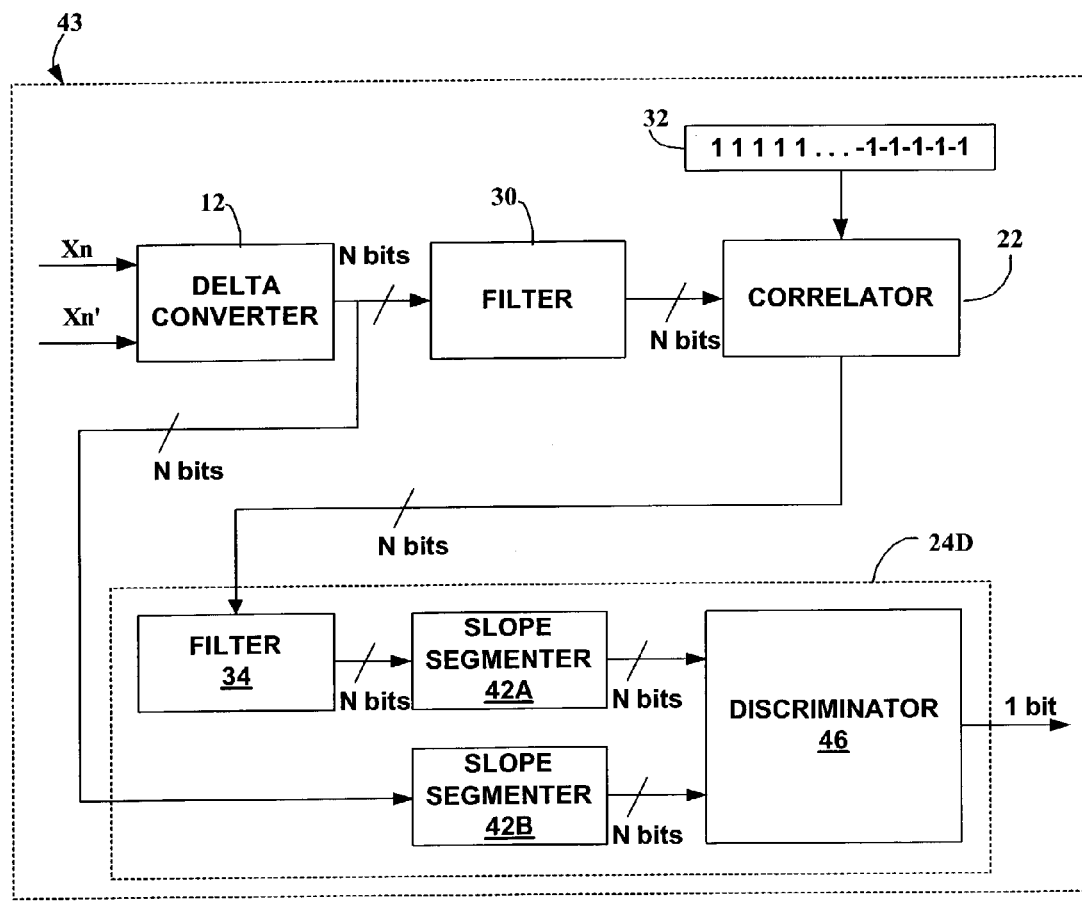
FIG. 5 is a block diagram of another exemplary device for electrically detecting cardiac p wave events.

FIG. 5 is a block diagram of another device 43 for electrically detecting cardiac p wave events. Device 43 conforms substantially to device 41 of FIG. 4, but further includes a pair of slope segmenters 42A, 42B. Slope segmenter 42A classifies the correlation output into different slope segments. Slope segmenter 42B, however, classifies the delta value produced by delta converter 12 into different slope segments. Discriminator 46 analyzes the slope segment values produced by both slope segmenters 42A, 42B in order to detect a p wave event.

Application of slope segmenters 42A, 42B to both the correlation output and the delta value improves the selectivity of discriminator 46 in detecting the p wave event. In particular, discriminator 46 applies independent sets of slope pattern criteria to the outputs of slope segmenters 42A, 42B. If both sets of slope pattern criteria indicate a p wave, the likelihood of correct identification of a p wave could be enhanced. Like device 41 of FIG. 4, device 43 supports rhythm classification, implementation of atrial aware ventricular pacing, and enhanced diagnostic data collection.

Figure 6:
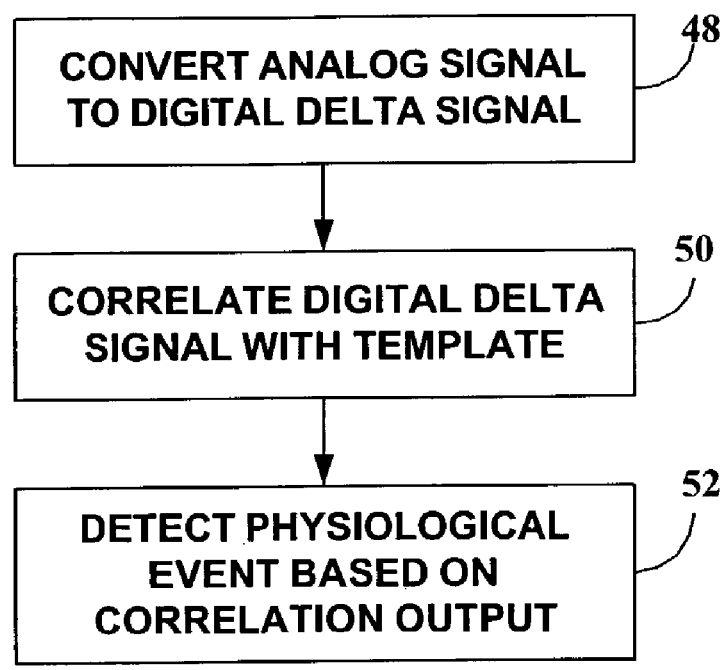
FIG. 6 is a flow diagram illustrating an exemplary method for electrically detecting physiological events.

FIG. 6 is a flow diagram illustrating a method for electrically detecting physiological events. As shown in FIG. 6, the method includes converting an analog signal to a digital delta value (48), and correlating the digital delta value with a correlation template (50). Upon correlation, the method further includes detecting a physiological event based on the correlation output (52).

Figure 7:
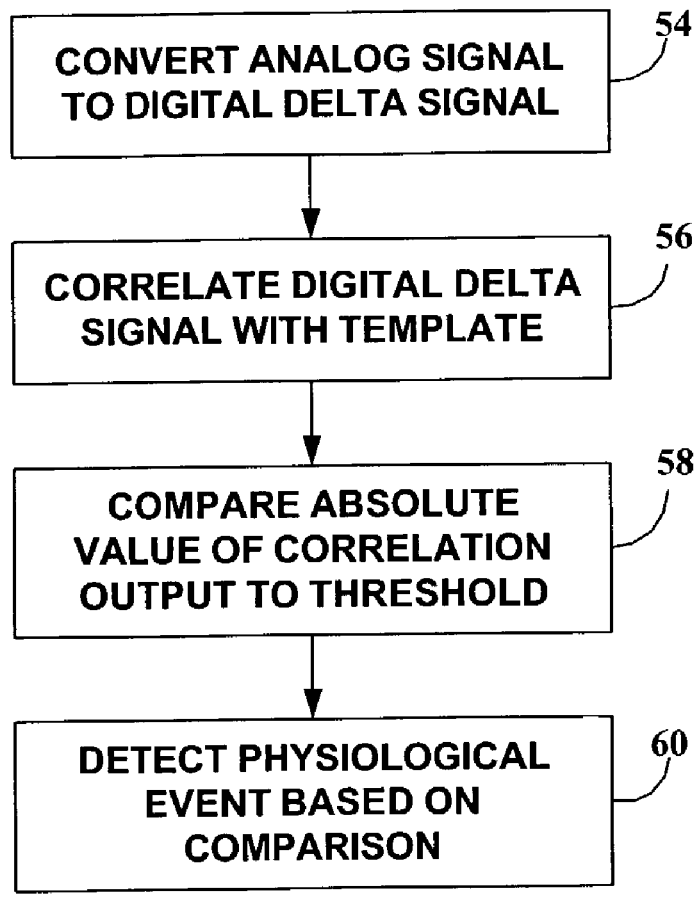
FIG. 7 is a flow diagram illustrating an exemplary method for electrically detecting cardiac R wave events.

FIG. 7 is a flow diagram illustrating a method for electrically detecting physiological events such as cardiac R wave events. As shown in FIG. 7, the method includes converting an analog signal to a digital delta value (54), and correlating the digital delta value with a correlation template (56). The method further includes comparing the absolute value of the correlation output to a threshold value (58). Based on the comparison, the method detects a physiological event such as a cardiac R wave event (60).

Figure 8:
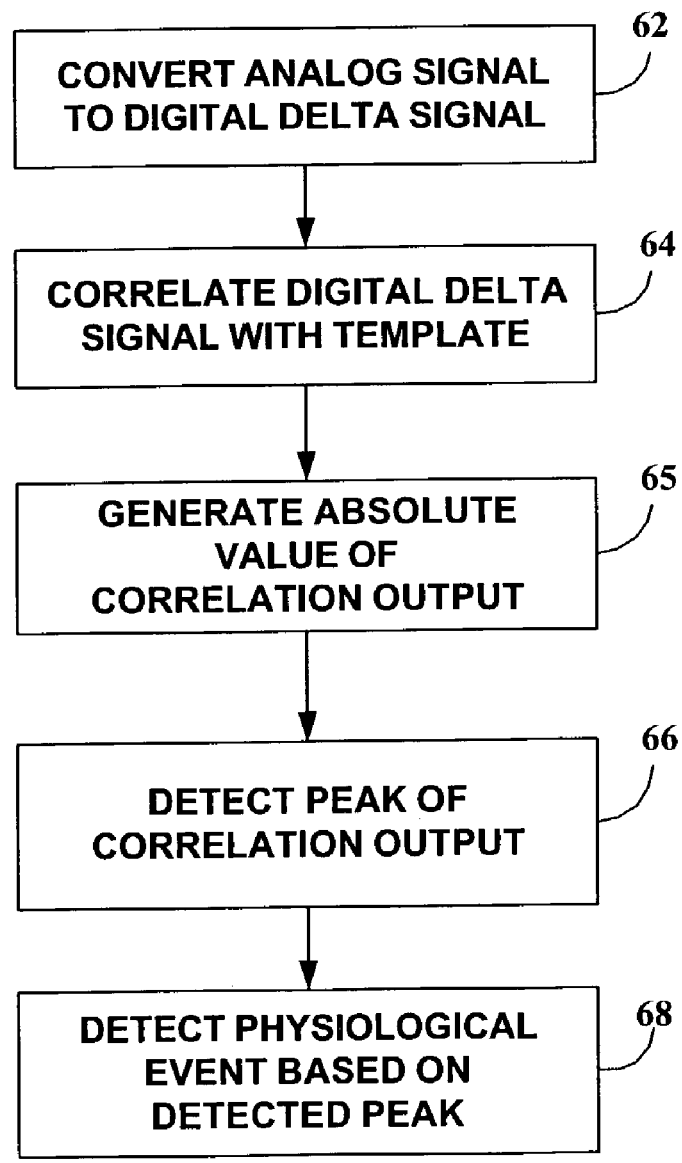
FIG. 8 is a flow diagram illustrating an exemplary method for electrically detecting respiratory events.

FIG. 8 is a flow diagram illustrating a method for electrically detecting respiratory events. As shown in FIG. 8, the method includes converting an analog signal to a digital delta value (62), and correlating the digital delta value with a correlation template (64). The method further includes generating an absolute value of the correlation output (65), and detecting the peak of the correlation output (66). Based on the detected peak, the method detects a physiological event in the form of a respiratory event (68).

Figure 9:
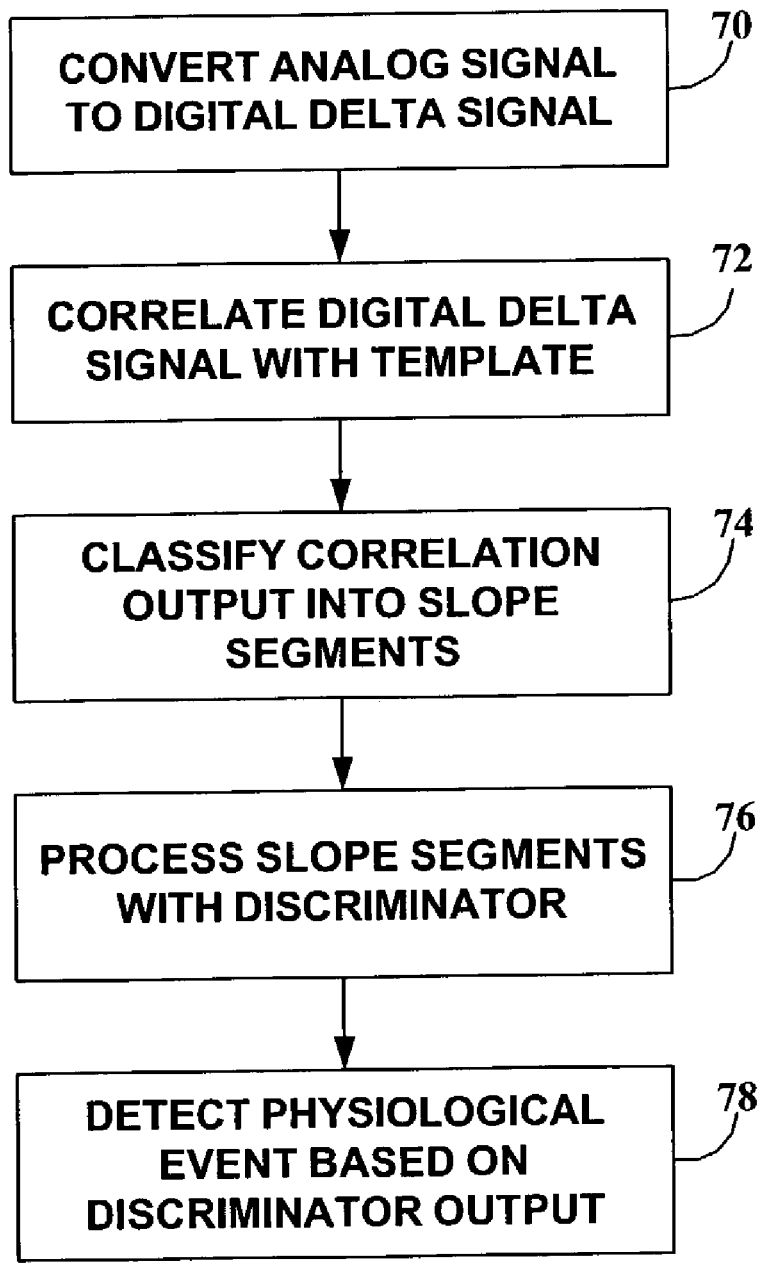
FIG. 9 is a flow diagram illustrating an exemplary method for electrically detecting cardiac p wave events.

FIG. 9 is a flow diagram illustrating a method for electrically detecting cardiac p wave events. As shown in FIG. 9, the method includes converting an analog signal to a digital delta value (70), and correlating the digital delta value with a correlation template (72). The method further includes classifying correlation output into slope segments (74), and processing the slope segments with a discriminator (76). Based on the discriminator output, the method detects a physiological event in the form of a p wave (78). In particular, the method involves comparison of the discriminator output to reference slope segment data for a typical p wave.

Figure 10:
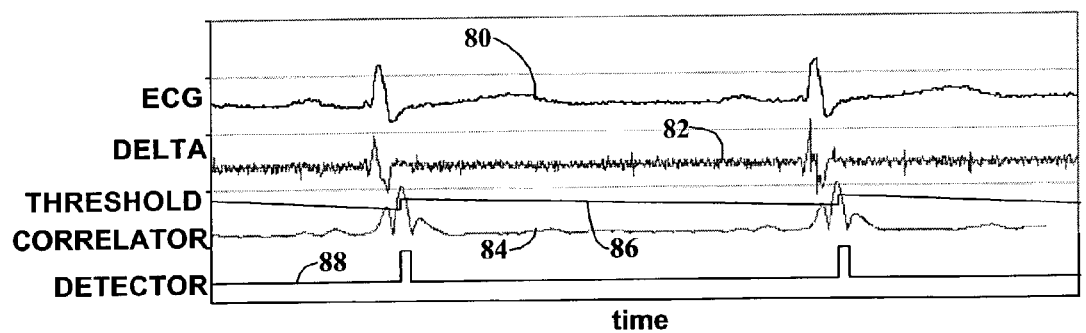
FIG. 10 is a graph illustrating operation of a device for electrically detecting physiological events.

FIG. 10 is a graph illustrating operation of device for electrically detecting physiological events. In particular, FIG. 10 illustrates detection of a cardiac R wave event using a digital correlation and a threshold comparison. In the graph of FIG. 10, reference numeral 80 identifies an ECG waveform, reference numeral 82 identifies a digital delta value 82, reference numeral 84 identifies a correlation output, and reference numeral 86 identifies a threshold applied to the correlation output to detect the presence of a cardiac R wave. Reference numeral 88 identifies the output of a detector that compares the correlation output to the threshold.

The invention provides one or more inventive features. For example, a detector constructed in accordance with the invention provides reliable electrical detection of physiological events such as cardiac R waves, cardiac p waves, or respiratory events. In addition, the detector provides reduced power consumption, reduced complexity, and ease of manufacturability. The detector may be configured to implement digital processing techniques that require relatively few external components and thereby permit ready integration of circuit components.

The detectors, including filters, correlators, and threshold circuits, may be realized entirely by digital circuitry and programmable functionality embodied in ASICs, FPGAs, DSPs, microprocessors, discrete logic circuitry, or the like. The input to the digital circuitry may come directly from a delta modulator front-end or from an amplifier/ADC combination. In the latter case, the digital circuits can generate the deltas by subtracting a previous ECG sample from a present ECG sample. The digital processing techniques permit reduced current consumption. As a further aspect of the invention, the detector implements adaptive thresholds that conform to different detection conditions, as described herein.

Some aspects of the invention may be embodied as a computer-readable medium that includes instructions for causing a programmable processor to carry out various aspects of the methods described above. A "computer-readable medium" includes but is not limited to read-only memory, Flash memory, and magnetic or optical storage media. The instructions may be implemented as one or more software or firmware modules, which may be executed by themselves or in combination with other modules.

The preceding specific embodiments are illustrative of the practice of the invention. Various modifications may be made without departing from the scope of the claims. For example, the invention may be practiced by a variety of implantable medical devices or external devices that monitor physiological events within a patient. These and other embodiments are within the scope of the following claims.

What is claimed is:

1. A physiological event detector comprising:
   a delta converter to convert an analog physiological signal to a digital delta value representative of a slope of the analog physiological signal;
   a correlator to correlate the digital delta value with a correlation template; and
   an event detector to detect a physiological event based on an output of the correlation circuit.

2. The detector of claim 1, wherein the physiological event is a cardiac event.

3. The detector of claim 2, wherein the cardiac event is an R wave.

4. The detector of claim 2, wherein the cardiac event is a p wave.

5. The detector of claim 1, wherein the physiological event is a respiratory event.

6. The detector of claim 1, wherein the event detection circuit includes a threshold detection circuit that compares the output of the correlation circuit to a threshold value and detects the physiological event based on the comparison.

7. The detector of claim 6, further comprising an absolute value circuit to produce an absolute value of the output of the correlation circuit, wherein the threshold detection circuit detects the physiological event if the absolute value of the output of the correlation circuit is greater than or equal to the threshold value.

8. The detector of claim 6, wherein the threshold detection circuit detects the physiological event when the output of the correlation circuit produces a first slope that exceeds the threshold followed by a second slope that exceeds the threshold within a window associated with the correlation template.

9. The detector of claim 1, wherein the event detection circuit includes a peak detection circuit that detects a peak of the output of the correlation circuit, and detects the physiological event in response to the detection of the peak.

10. The detector of claim 9, further comprising an absolute value circuit to produce an absolute value of the output of the correlation circuit, wherein the peak detection circuit detects the physiological event based on the absolute value of the output of the correlation circuit.

11. The detector of claim 9, wherein the peak detection circuit detects the physiological event when the output of the correlation circuit produces a positive peak slope followed by a negative peak slope within a window associated with the correlation template.

12. The detector of claim 1, wherein the event detection circuit includes a slope segmenter that classifies the output of the correlation circuit into slope segments, and a discrimination circuit that analyzes the slope segments to detect the physiological event.

13. The detector of claim 12, wherein the discriminator detects p waves based on widths of the slope segments.

14. The detector of claim 1, further comprising a smoothing filter to smooth the digital delta value.

15. The detector of claim 1, wherein the digital delta value forms an input vector, the correlation template forms a slope template vector, and the output of the correlation circuit is a sum of a product of the input vector and the slope template vector over a plurality of samples of the digital delta value.

16. A method comprising:
   converting an analog physiological signal to a digital delta value representative of a slope of the analog physiological signal;
   correlating the digital delta value with a correlation template; and
   detecting a physiological event based on an output of the correlation.

17. The method of claim 16, wherein the physiological event is a cardiac event.

18. The method of claim 17, wherein the cardiac event is an R wave.

19. The method of claim 17, wherein the cardiac event is a p wave.

20. The method of claim 16, wherein the physiological event is a respiratory event.

21. The method of claim 16, further comprising comparing the output of the correlation to a threshold value and detecting the physiological event based on the comparison.

22. The method of claim 21, further comprising producing an absolute value of the output of the correlation, and detecting the physiological event if the absolute value of the output of the correlation is greater than or equal to the threshold value.

23. The method of claim 21, wherein detecting the physiological event includes detecting the physiological event when the output of the correlation circuit produces a first slope that exceeds the threshold followed by a second slope that exceeds the threshold within a window associated with the correlation template.

24. The method of claim 16, further comprising detecting a peak of the output of the correlation, and detecting the physiological event in response to the detection of the peak.

25. The method of claim 24, further comprising producing an absolute value of the output of the correlation, and detecting the physiological event based on the absolute value of the output of the correlation.

26. The method of claim 24, further comprising detecting the physiological event when the output of the correlation produces a positive peak slope followed by a negative peak slope within a window associated with the correlation template.

27. The method of claim 16, further comprising classifying the output of the correlation into slope segments, and analyzing the slope segments to detect the physiological event.

28. The method of claim 27, further comprising detecting p waves based on widths of the slope segments.

29. The method of claim 16, further comprising a smoothing the digital delta value with a smoothing filter.

30. The method of claim 16, wherein the digital delta value forms an input vector, the correlation template forms a slope template vector, and the output of the correlation is a sum of a product of the input vector and the slope template vector over a plurality of samples of the digital delta value.

31. A physiological event detector comprising:
means for converting an analog physiological signal to a digital delta value representative of a slope of the analog physiological signal;
means for correlating the digital delta value with a correlation template; and
means for detecting a physiological event based on an output of the correlation.

32. The detector of claim 31, wherein the physiological event is a cardiac event.

33. The detector of claim 32, wherein the cardiac event is an R wave.

34. The detector of claim 32, wherein the cardiac event is a p wave.

35. The detector of claim 31, wherein the physiological event is a respiratory event.

36. The detector of claim 31, further comprising comparing the output of the correlation to a threshold value and detecting the physiological event based on the comparison.

37. The detector of claim 36, further comprising means for producing an absolute value of the output of the correlation, and means for detecting the physiological event if the absolute value of the output of the correlation is greater than or equal to the threshold value.

38. The detector of claim 36, wherein the means for detecting the physiological event includes means for detecting the physiological event when the output of the correlation circuit produces a first slope that exceeds the threshold followed by a second slope that exceeds the threshold within a window associated with the correlation template.

39. The detector of claim 31, further comprising means for detecting a peak of the output of the correlation, and means for detecting the physiological event in response to the detection of the peak.

40. The detector of claim 39, further comprising means for producing an absolute value of the output of the correlation, and means for detecting the physiological event based on the absolute value of the output of the correlation.

41. The detector of claim 39, further comprising means for detecting the physiological event when the output of the correlation produces a positive peak slope followed by a negative peak slope within a window associated with the correlation template.

42. The detector of claim 31, further comprising means for classifying the output of the correlation into slope segments, and means for analyzing the slope segments to detect the physiological event.

43. The detector of claim 42, further comprising means for detecting p waves based on widths of the slope segments.

44. The detector of claim 31, further comprising means for smoothing the digital delta value with a smoothing filter.

45. The detector of claim 31, wherein the digital delta value forms an input vector, the correlation template forms a slope template vector, and the output of the correlation is a sum of a product of the input vector and the slope template vector over a plurality of samples of the digital delta value.

* * * * *